United States Patent
Lee et al.

(10) Patent No.: US 10,987,335 B2
(45) Date of Patent: *Apr. 27, 2021

(54) PHARMACEUTICAL COMPOSITION FOR ORAL ADMINISTRATION COMPRISING HIGH CONCENTRATION TAXANE

(71) Applicant: DAE HWA PHARMA. CO., LTD., Gangwon-do (KR)

(72) Inventors: In-Hyun Lee, Gwangju (KR); Min-Hee Son, Uiwang-si (KR); Yeong-Taek Park, Ansan-si (KR); Han-Koo Lee, Seoul (KR)

(73) Assignee: DAE HWA PHARMA. CO., LTD., Gangwon-do (KR)

( * ) Notice: Subject to any disclaimer, the term of this patent is extended or adjusted under 35 U.S.C. 154(b) by 453 days.

This patent is subject to a terminal disclaimer.

(21) Appl. No.: 15/748,722

(22) PCT Filed: Apr. 6, 2016

(86) PCT No.: PCT/KR2016/003558
§ 371 (c)(1),
(2) Date: Jan. 30, 2018

(87) PCT Pub. No.: WO2017/018635
PCT Pub. Date: Feb. 2, 2017

(65) Prior Publication Data
US 2020/0085780 A1 Mar. 19, 2020

(30) Foreign Application Priority Data

Jul. 30, 2015 (KR) .......... 10-2015-0108004
Jul. 30, 2015 (KR) .......... 10-2015-0108008

(51) Int. Cl.
  *A61K 31/337* (2006.01)
  *A61K 9/00* (2006.01)
  *A61K 47/10* (2017.01)
  *A61K 47/14* (2017.01)

(52) U.S. Cl.
CPC .......... *A61K 31/337* (2013.01); *A61K 9/0053* (2013.01); *A61K 47/10* (2013.01); *A61K 47/14* (2013.01)

(58) Field of Classification Search
CPC .... A61K 31/337; A61K 9/0053; A61K 47/10; A61K 47/14; A61K 9/1075; A61K 47/30; A61K 31/335; A61K 9/00
See application file for complete search history.

(56) References Cited

U.S. PATENT DOCUMENTS

| 6,979,456 | B1 | 12/2005 | Parikh et al. |
| 8,075,917 | B2 | 12/2011 | Chung et al. |
| 2004/0092428 | A1 | 5/2004 | Chen et al. |
| 2006/0104999 | A1 | 5/2006 | Chung et al. |
| 2010/0310661 | A1 | 12/2010 | Chen et al. |

FOREIGN PATENT DOCUMENTS

| KR | 10-2007-0058776 A | | 6/2007 |
| WO | 02/064132 A2 | | 8/2002 |
| WO | WO03045357 | * | 6/2003 |
| WO | WO 2003045357 | * | 6/2005 |

OTHER PUBLICATIONS

Ahmad et al., "Solid-Nanoemulsion Preconcentrate for Oral Delivery of Paclitaxel: Formulation Design, Biodistribution, and γ Scintigraphy Imaging", BioMed Research International, 2014, Article ID 984756, 1-12 pages, (2014).
Huizing et al., "Taxanes: A New Class of Antitumor Agents", Cancer Inv., 1995, 13: 381-404.
Eiseman et al, Second NCI Workshop on Taxol and Taxus (Sep. 1992), Suffness (ed.) et al, TaxolTM Science and Applications, CRC Press (1995).
Walle et al, "Taxol Transport by Human Intestinal Epithelial CACO-2 Cells", Drug Metabo. Disp. 26(4): 343-346 (1998).
The extended European Search Report in corresponding EP Application No. 16830669.4, dated Nov. 26, 2018, six pages.

* cited by examiner

*Primary Examiner* — Snigdha Maewall
(74) *Attorney, Agent, or Firm* — Vorys, Sater, Seymour & Pease LLP; Mih Suhn Koh (57) ABSTRACT

The present invention provides a pharmaceutical composition for oral administration, consisting essentially of (a) 4 to 40% by weight of a taxane, (b) 10 to 40% by weight of polyoxyl glyceryl fatty acid ester, (c) 30 to 70% by weight of monooleoyl glycerol or 30 to 70% by weight of an oleoyl glycerol complex having 30 to 65% by weight of monooleoyl glycerol contents; 15 to 50% by weight of dioleoyl glycerol contents; and 2 to 20% by weight of trioleoyl glycerol contents, and (d) 5 to 30% by weight of a surfactant and a process for preparing the same.

15 Claims, 3 Drawing Sheets

PHARMACEUTICAL COMPOSITION FOR ORAL ADMINISTRATION COMPRISING HIGH CONCENTRATION TAXANE

TECHNICAL FIELD

The present invention relates to a pharmaceutical composition for oral administration comprising a taxane in a high concentration. More specifically, the present invention relates to a taxane-containing pharmaceutical composition for oral administration comprising polyoxyl glyceryl fatty acid ester.

BACKGROUND ART

Taxanes, which are an anticancer agent showing their anti-proliferative effect by acting on the organization of the microtubules in the cellular cytoskeletal system (Huizing M. T. et al., Cancer Inv., 1995, 13: 381-404), are known to exhibit excellent cytotoxicity against various kinds of cancers such as ovarian cancer, breast cancer, esophagus cancer, melanoma and leukemia. Parenteral dosage forms of paclitaxel and docetaxel are commercially available under the trademarks Taxol™ and Taxotere™, respectively. Since a taxane is known to have very low water solubility, the currently available paclitaxel-containing formulation, e.g., Taxol™, has been formulated into the form of emulsion preconcentrate, which is diluted before using for injection. However, in order to overcome the problems related to patient compliance due to the use of the injection form, stability of the formulation, and safety to the human body, etc., researches on the formulations for oral administration are being carried out.

Meanwhile, it has been reported that the oral administration of a taxane such as paclitaxel exhibits very low oral bioavailability due to the action of an outwardly directed efflux pump (Walle et al, Drug Metabo. Disp. 26(4): 343-346 (1998)). It has been also reported that the orally administered paclitaxel is very poorly absorbed (less than 1%) (Eiseman et al, Second NCI Workshop on Taxol and Taxus (September 1992), Suffness (ed.) et al, Taxol™ Science and Applications, CRC Press (1995)). As an attempt to improve such a low oral bioavailability, Korean Patent Publication No. 10-2004-0009015 has disclosed a solubilized taxane-containing composition for oral administration, which is formulated by using a medium chain triglyceride such as triacetin, a monoglyceride such as monoolein, and a surfactant such as Tween. Said composition is a solubilized taxane-containing composition for oral administration, whose bioavailability is increased through high mucoadhesive property in the intestine by the monoglyceride such as monoolein. And also, Korean Patent Publication No. 10-2007-0058776 has disclosed an improved process for preparing the solubilized taxane-containing composition for oral administration, the process comprising dissolving paclitaxel, along with a medium chain triglyceride, a monoglyceride, and surfactant, in an organic solvent.

Solid formulations such as soft capsules have advantages in terms of the ease of use, compared to the lipid solution form. Considering the patient's compliance, it is necessary to control the size of the soft capsules to an appropriate size. Therefore, in order to prepare a soft capsule containing the therapeutically effective amount of a taxane, it is required to prepare a lipid solution containing the taxane in a high concentration. However, when a taxane is contained in a high concentration (for example, 4% by weight or more) according to conventional formulation methods (e.g., Korean Patent Publication Nos. 10-2004-0009015 and 10-2007-0058776), the taxane is precipitated from the lipid solution and thus the completely solubilized lipid solution cannot be obtained, thereby leading to the problem of decreased bioavailability.

DISCLOSURE

Technical Problem

The present inventors carried out various researches in order to develop a pharmaceutical composition for oral administration, for example in a capsule form, comprising a taxane in a high concentration. The present inventors have found that, when formulation processes are performed by using polyoxyl glyceryl fatty acid ester, instead of the medium chain triglyceride which is one of the essential element in the conventional paclitaxel-containing compositions (e.g., the compositions prepared according to Korean Patent Publication Nos. 10-2004-0009015 and 10-2007-0058776), a clear solution containing a taxane in a high concentration can be obtained, thereby being able to be formulated into a capsule form such as a soft capsule without the formation of a precipitate.

A conventional solubilized paclitaxel-containing composition for oral administration (for example, the compositions prepared according to Korean Patent Publication Nos. 10-2004-0009015 and 10-2007-0058776) is stored under refrigerated conditions in the semi-solid form, which is converted into a solution form at the time of use and then is orally administered to a patient. However, the composition stored under refrigerated conditions in the semi-solid form is not converted to a solution at room temperature, and also still exists in the semi-solid form even when it is allowed to stand for a long time. Therefore, in order to convert to the solution form that can be administered to a patient, there is a problem that additional processing through heating should be performed.

The present inventors carried out various researches in order to solve the problems. Surprisingly, the present inventors have found that, when formulation processes are performed by using a certain oleoyl glycerol complex instead of the monoglyceride, the resulting formulations are present in a solution form at room temperature and thus can be administered directly to a patient without additional processing such as heating. In addition, the present inventors have found that the compositions formulated by using the oleoyl glycerol complex effectively allow to increase the in vivo absorption rate, in comparison with the conventional composition obtained by using a monoglyceride such as monoolein. Especially, it has been found that the capsules formulated through the combination of polyoxyl glyceryl fatty acid ester and the oleoyl glycerol complex, instead of the medium chain triglyceride, are quickly absorbed from the beginning and represent a remarkably increased in vivo absorption rate.

Therefore, it is an object of the present invention to provide a taxane-containing pharmaceutical composition for oral administration which is formulated by using polyoxyl glyceryl fatty acid ester as a solubilizing agent.

And also, it is another object of the present invention to provide a process for preparing the pharmaceutical composition for oral administration.

Technical Solution

In accordance with an aspect of the present invention, there is provided a pharmaceutical composition for oral administration, consisting essentially of (a) 4 to 40% by weight of a taxane, (b) 10 to 40% by weight of polyoxyl glyceryl fatty acid ester, (c) (c-1) 30 to 70% by weight of monooleoyl glycerol or (c-2) 30 to 70% by weight of an oleoyl glycerol complex having 30 to 65% by weight of monooleoyl glycerol contents; 15 to 50% by weight of dioleoyl glycerol contents; and 2 to 20% by weight of trioleoyl glycerol contents, and (d) 5 to 30% by weight of a surfactant.

In an embodiment, the oleoyl glycerol complex has 32 to 52% by weight of monooleoyl glycerol contents; 30 to 50% by weight of dioleoyl glycerol contents; and 5 to 20% by weight of trioleoyl glycerol contents. In another embodiment, the oleoyl glycerol complex has 55 to 65% by weight of monooleoyl glycerol contents; 15 to 35% by weight of dioleoyl glycerol contents; and 2 to 10% by weight of trioleoyl glycerol contents. In still another embodiment, the polyoxyl glyceryl fatty acid ester may be one or more selected from the group consisting of caprylocaproyl polyoxyl glyceride, lauroyl polyoxyl glyceride, and stearoyl polyoxyl glyceride.

In accordance with another aspect of the present invention, there is provided a process for preparing a pharmaceutical composition for oral administration, comprising (i) dissolving (a) 4 to 40% by weight of a taxane and (b) 10 to 40% by weight of polyoxyl glyceryl fatty acid ester in an organic solvent, (ii) removing the organic solvent from the solution obtained in Step (i), followed by mixing (c-1) 30 to 70% by weight of monooleoyl glycerol or (c-2) 30 to 70% by weight of an oleoyl glycerol complex having 30 to 65% by weight of monooleoyl glycerol contents; 15 to 50% by weight of dioleoyl glycerol contents; and 2 to 20% by weight of trioleoyl glycerol contents, and (d) 5 to 30% by weight of a surfactant therewith to form a solution, and (iii) optionally, filling the solution obtained in Step (ii) in a capsule.

In accordance with still another aspect of the present invention, there is provided a process for preparing a pharmaceutical composition for oral administration, comprising (i') dissolving (a) 4 to 40% by weight of a taxane, (b) 10 to 40% by weight of polyoxyl glyceryl fatty acid ester, (c-1) 30 to 70% by weight of monooleoyl glycerol or (c-2) 30 to 70% by weight of an oleoyl glycerol complex having 30 to 65% by weight of monooleoyl glycerol contents; 15 to 50% by weight of dioleoyl glycerol contents; and 2 to 20% by weight of trioleoyl glycerol contents, and (d) 5 to 30% by weight of a surfactant in an organic solvent, (ii') removing the organic solvent from the solution obtained in Step (i'), and (iii') optionally, filling the solution obtained in Step (ii') in a capsule.

Advantageous Effects

It has been found by the present invention that, when formulation processes are performed by using polyoxyl glyceryl fatty acid ester instead of the medium chain triglyceride in a lipid solution comprising a taxane, a medium chain triglyceride, monooleoyl glycerol, and a surfactant, a clear solution containing a taxane in a high concentration can be obtained, thereby being able to be formulated into a capsule form such as a soft capsule without the formation of a precipitate. Therefore, the pharmaceutical composition for oral administration according to the present invention makes it possible to formulate into solid formulations such as soft capsules.

And also, it has been found by the present invention that a solubilized taxane-containing composition for oral administration remarkably varies in the form and/or appearance thereof according to the types and/or properties of the lipid used. Especially, it has been found by the present invention that, when formulation processes are performed by using a certain oleoyl glycerol complex, the resulting formulations are present in a solution form at room temperature and thus can be administered directly to a patient without additional processing such as heating. In addition, it has been found by the present invention that the compositions formulated by using the oleoyl glycerol complex effectively allow to increase the in vivo absorption rate, in comparison with the conventional composition obtained by using a monoglyceride such as monoolein. Especially, it has been found by the present invention that the capsules formulated through the combination of polyoxyl glyceryl fatty acid ester and the oleoyl glycerol complex, instead of the medium chain triglyceride, are quickly absorbed from the beginning and represent a remarkably increased in vivo absorption rate. Therefore, the pharmaceutical composition for oral administration according to the present invention can solve the problems of the conventional formulations that additional solubilizing processing should be carried out at the time of use; and effectively increase the in vivo absorption rate of the taxane.

DESCRIPTION OF DRAWINGS

FIG. 1 represents the appearance of the docetaxel-containing lipid solution prepared in Example 10.

BEST MODE

The present invention provides a pharmaceutical composition for oral administration, consisting essentially of (a) 4 to 40% by weight of a taxane, (b) 10 to 40% by weight of polyoxyl glyceryl fatty acid ester, (c) (c-1) 30 to 70% by weight of monooleoyl glycerol or (c-2) 30 to 70% by weight of an oleoyl glycerol complex having 30 to 65% by weight of monooleoyl glycerol contents; 15 to 50% by weight of dioleoyl glycerol contents; and 2 to 20% by weight of trioleoyl glycerol contents, and (d) 5 to 30% by weight of a surfactant.

It has been found by the present invention that, when formulation processes are performed by using polyoxyl glyceryl fatty acid ester instead of the medium chain triglyceride in a lipid solution comprising a taxane, a medium chain triglyceride, monooleoyl glycerol, and a surfactant, a clear solution containing a taxane in a high concentration can be obtained, thereby being able to be formulated into a capsule form such as a soft capsule without the formation of a precipitate.

The polyoxyl glyceryl fatty acid ester may be one or more selected from the group consisting of caprylocaproyl polyoxyl glyceride, lauroyl polyoxyl glyceride, and stearoyl polyoxyl glyceride. Preferably, the polyoxyl glyceryl fatty acid ester may be one or more selected from the group consisting of caprylocaproyl polyoxyl-32 glyceride (e.g., LABRASOL™, etc.), lauroyl polyoxyl-32 glyceride (e.g., Gelucire™ 44/14, etc.), and stearoyl polyoxyl-32 glyceride (e.g., Gelucire™ 50/13, etc.).

The monooleoyl glycerol is also referred to as monoolein. A commercially available monooleoyl glycerol (e.g., Rylo MG 19™, Danisco) may be also used.

It has been found by the present invention that a solubilized taxane-containing composition for oral administration remarkably varies in the form and/or appearance thereof according to the types and/or properties of the lipid used. Especially, it has been found by the present invention that, when formulation processes are performed by using a certain oleoyl glycerol complex, the resulting formulations are present in a solution form at room temperature and thus can be administered directly to a patient without additional processing such as heating. In addition, it has been found by the present invention that the compositions formulated by using the oleoyl glycerol complex effectively allow to increase the in vivo absorption rate, in comparison with the conventional composition obtained by using a monoglyceride such as monoolein. Especially, it has been found by the present invention that the capsules formulated through the combination of polyoxyl glyceryl fatty acid ester and the oleoyl glycerol complex, instead of the medium chain triglyceride, are quickly absorbed from the beginning and represent a remarkably increased in vivo absorption rate.

As used herein, the term "oleoyl glycerol complex" refers to a mixture obtained by partial glycerolysis of vegetable oils mainly containing triacylglycerols of oleic acid or by esterification of glycerol by oleic acid. The respective contents of monooleoyl glycerol, dioleoyl glycerol and trioleoyl glycerol therein vary according to the partial glycerolysis and/or esterification. An oleoyl glycerol complex having a certain content ratio is used in the present invention. That is, there is used in the present invention an oleoyl glycerol complex having 30 to 65% by weight of monooleoyl glycerol contents; 15 to 50% by weight of dioleoyl glycerol contents; and 2 to 20% by weight of trioleoyl glycerol contents. In an embodiment, the oleoyl glycerol complex has 32 to 52% by weight of monooleoyl glycerol contents; 30 to 50% by weight of dioleoyl glycerol contents; and 5 to 20% by weight of trioleoyl glycerol contents. In another embodiment, the oleoyl glycerol complex has 55 to 65% by weight of monooleoyl glycerol contents; 15 to 35% by weight of dioleoyl glycerol contents; and 2 to 10% by weight of trioleoyl glycerol contents. In addition, a commercially available oleoyl glycerol complex having said content ratio, e.g., PECEOL™ (Gattefosse) or CAPMUL™ (Abitec) may be also used.

In the pharmaceutical composition for oral administration of the present invention, the taxane includes one or more selected from the group consisting of paclitaxel, docetaxel, 7-epipaclitaxel, t-acetylpaclitaxel, 10-desacetylpaclitaxel, 10-desacetyl-7-epipaclitaxel, 7-xylosylpaclitaxel, 10-desacetyl-7-glutarylpaclitaxel, 7-N,N-dimethylglycylpaclitaxel, 7-L-alanylpaclitaxel, and so on. For example, the taxane may be paclitaxel and/or docetaxel, preferably paclitaxel.

The surfactant includes polyoxyethylene-polyoxypropylene block copolymer (e.g., Poloxamer™), sorbitan ester (e.g., Span™), polyoxyethylene sorbitan (e.g., Tween™), polyoxyethylene ether (e.g., Brij™), and so on.

In an embodiment, the pharmaceutical composition of the present invention may consist essentially of 4 to 35% by weight of the taxane, 15 to 30% by weight of polyoxyl glyceryl fatty acid ester, 35 to 60% by weight of monooleoyl glycerol or 35 to 60% by weight of the oleoyl glycerol complex, and 10 to 25% by weight of the surfactant. The pharmaceutical composition for oral administration is preferably in the form filled in a capsule such as a soft capsule.

In accordance with another aspect of the present invention, there is provided a process for preparing a pharmaceutical composition for oral administration, comprising (i) dissolving (a) 4 to 40% by weight of a taxane and (b) 10 to 40% by weight of polyoxyl glyceryl fatty acid ester in an organic solvent, (ii) removing the organic solvent from the solution obtained in Step (i), followed by mixing (c-1) 30 to 70% by weight of monooleoyl glycerol or (c-2) 30 to 70% by weight of an oleoyl glycerol complex having 30 to 65% by weight of monooleoyl glycerol contents; 15 to 50% by weight of dioleoyl glycerol contents; and 2 to 20% by weight of trioleoyl glycerol contents, and (d) 5 to 30% by weight of a surfactant therewith to form a solution, and (iii) optionally, filling the solution obtained in Step (ii) in a capsule.

In accordance with still another aspect of the present invention, there is provided a process for preparing a pharmaceutical composition for oral administration, comprising (i') dissolving (a) 4 to 40% by weight of a taxane, (b) 10 to 40% by weight of polyoxyl glyceryl fatty acid ester, (c-1) 30 to 70% by weight of monooleoyl glycerol or (c-2) 30 to 70% by weight of an oleoyl glycerol complex having 30 to 65% by weight of monooleoyl glycerol contents; 15 to 50% by weight of dioleoyl glycerol contents; and 2 to 20% by weight of trioleoyl glycerol contents, and (d) 5 to 30% by weight of a surfactant in an organic solvent, (ii') removing the organic solvent from the solution obtained in Step (i'), and (iii') optionally, filling the solution obtained in Step (ii') in a capsule.

In the processes of the present invention, said monooleoyl glycerol, oleoyl glycerol complex, taxane, surfactant, and polyoxyl glyceryl fatty acid ester are as described above.

In the processes of the present invention, the organic solvent may be one or more selected from the group consisting of a halogenated alkyl compound, an alcohol, and a ketone. The halogenated alkyl compound may be one or more selected from the group consisting of halogenated $C_1$ to $C_5$ alkyl compounds, preferably methylene chloride or chloroform, more preferably methylene chloride. The alcohol may be one or more selected from the group consisting of $C_1$ to $C_5$ lower alcohols, preferably methanol, ethanol or isopropyl alcohol, more preferably ethanol. The ketone may be acetone.

The organic solvent may be used in an amount capable of dissolving the taxane and the polyoxyl glyceryl fatty acid ester, preferably in the amount of 0.4 times to 20 times based on the volume of the polyoxyl glyceryl fatty acid ester, more preferably in the same volume as the volume of the polyoxyl glyceryl fatty acid ester, but is not limited thereto. Said amounts of the organic solvent, which makes it possible to dissolve the taxane such as paclitaxel and docetaxel sufficiently, can reduce the waste originated from the use of excessive amounts of the solvent and the unnecessary effort for removing the organic solvent. In the processes of the present invention, the step for removing the organic solvent may be performed according to conventional drying methods, for example, by drying under reduced pressure at 15 to 50° C., preferably at room temperature. Through performing the steps for dissolving with an organic solvent and removing the organic solvent as described above, it is possible to homogeneously mix the respective components in the resulting composition.

The present invention will be described in further detail with reference to the following examples and experimental examples. These examples and experimental examples are for illustrative purposes only and are not intended to limit the scope of the present invention.

Example 1. Docetaxel-Containing Soft Capsules

Figure 1:
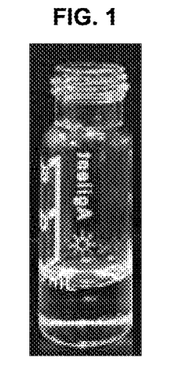
FIG. 1 represents the appearance of the docetaxel-containing lipid solution prepared in Example 1.

The docetaxel-containing pharmaceutical composition for oral administration was prepared according to the components and amounts shown in Table 1. Docetaxel and LABRASOL™ (Gattefosse) were completely dissolved in methylene chloride (about 14 times of the volume of LABRASOL™). The resulting solution was dried under reduced pressure at 40° C. to remove methylene chloride. To the resulting mixture, were added monooleoyl glycerol (Rylo MG 19™, Danisco) and Tween™ 80. The resulting mixture was stirred at 40° C. to obtain the clear oily solution. The resulting clear oily solution was filled into a soft capsule. The appearance of the oily solution is shown in FIG. 1.

TABLE 1

| | L/I | Component | Amount/ 1 capsule | Ratio (% by weight) |
|---|---|---|---|---|
| 1 | Taxane | Docetaxel | 50 mg | 4.72 |
| 2 | Polyoxyl glyceryl fatty acid ester | LABRASOL ™ | 0.28 ml | 27.94 |
| 3 | Monooleoyl glycerol | Rylo MG 19 ™ | 0.56 ml | 50.35 |
| 4 | Surfactant | Tween ™ 80 | 0.16 ml | 16.99 |
| | | Total | | 100.00 |

Example 2

The docetaxel-containing pharmaceutical composition for oral administration in the soft capsule form was prepared in accordance with the same procedures as in Example 1, using Gelucire™ 44/14 (Gettafosse) instead of LABRASOL™.

Example 3

The docetaxel-containing pharmaceutical composition for oral administration in the soft capsule form was prepared in accordance with the same procedures as in Example 1, using Gelucire™ 50/13 (Gettafosse) instead of LABRASOL™.

Example 4

The docetaxel-containing pharmaceutical composition for oral administration in the soft capsule form was prepared in accordance with the same procedures as in Example 1, using anhydrous ethanol instead of methylene chloride.

Example 5. Paclitaxel-Containing Soft Capsules

Figure 2:
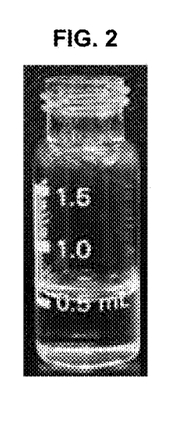
FIG. 2 represents the appearance of the paclitaxel-containing lipid solution prepared in Example 5.

The paclitaxel-containing pharmaceutical composition for oral administration was prepared according to the components and amounts shown in Table 2. Paclitaxel and LABRASOL™ (Gattefosse) were completely dissolved in methylene chloride (about 14 times of the volume of LABRASOL™). The resulting solution was dried under reduced pressure at 40° C. to remove methylene chloride. To the resulting mixture, were added monooleoyl glycerol (Rylo MG 19™, Danisco) and Tween™ 80. The resulting mixture was stirred at 40° C. to obtain the clear oily solution. The resulting clear oily solution was filled into a soft capsule. The appearance of the oily solution is shown in FIG. 2.

TABLE 2

| | L/I | Component | Amount/ 1 capsule | Ratio (% by weight) |
|---|---|---|---|---|
| 1 | Taxane | Paclitaxel | 70 mg | 6.49 |
| 2 | Polyoxyl glyceryl fatty acid ester | LABRASOL ™ | 0.28 ml | 27.41 |
| 3 | Monooleoyl glycerol | Rylo MG 19 ™ | 0.56 ml | 49.42 |
| 4 | Surfactant | Tween ™ 80 | 0.16 ml | 16.68 |
| | | Total | | 100.00 |

Example 6

The paclitaxel-containing pharmaceutical composition for oral administration in the soft capsule form was prepared in accordance with the same procedures as in Example 5, using anhydrous ethanol instead of methylene chloride.

Example 7

The paclitaxel-containing pharmaceutical composition for oral administration in the soft capsule form was prepared in accordance with the same procedures as in Example 5, using Gelucire™ 44/14 (Gettafosse) instead of LABRASOL™.

Example 8

The paclitaxel-containing pharmaceutical composition for oral administration in the soft capsule form was prepared in accordance with the same procedures as in Example 5, using Gelucire™ 50/13 (Gettafosse) instead of LABRASOL™.

Example 9. Paclitaxel-Containing Soft Capsules

The paclitaxel-containing pharmaceutical composition for oral administration was prepared according to the components and amounts shown in Table 3. Paclitaxel and LABRASOL™ (Gattefosse) were completely dissolved in methylene chloride (about 14 times of the volume of LABRASOL™). The resulting solution was dried under reduced pressure at 40° C. to remove methylene chloride. To the resulting mixture, were added monooleoyl glycerol (Rylo MG 19™, Danisco) and Tween™ 80. The resulting mixture was stirred at 40° C. to obtain the clear oily solution. The resulting clear oily solution was filled into a soft capsule.

TABLE 3

| | L/I | Component | Amount/ 1 capsule | Ratio (% by weight) |
|---|---|---|---|---|
| 1 | Taxane | Paclitaxel | 500 mg | 34.09 |
| 2 | Polyoxyl glyceryl fatty acid ester | LABRASOL ™ | 0.28 ml | 17.99 |

TABLE 3-continued

| L/I | Component | Amount/ 1 capsule | Ratio (% by weight) |
|---|---|---|---|
| 3 | Monooleoyl glycerol | Rylo MG 19 ™ | 0.56 ml | 36.26 |
| 4 | Surfactant | Tween ™ 80 | 0.16 ml | 11.66 |
| | Total | | 100.00 |

Example 10. Docetaxel-Containing Soft Capsules

Figure 3:
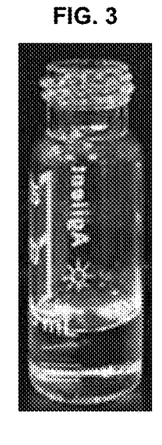

The docetaxel-containing pharmaceutical composition for oral administration was prepared according to the components and amounts shown in Table 4. Docetaxel and LABRASOL™ (Gattefosse) were completely dissolved in ethanol (about 14 times of the volume of LABRASOL™). The resulting solution was dried under reduced pressure at 40° C. to remove ethanol. To the resulting mixture, were added PECEOL™ (Gattefosse) and Tween™ 80. The resulting mixture was stirred at 40° C. to obtain the clear oily solution. The resulting clear oily solution was filled into a soft capsule. The appearance of the oily solution is shown in FIG. 3.

TABLE 4

| L/I | Component | Amount/ 1 capsule | Ratio (% by weight) |
|---|---|---|---|
| 1 | Taxane | Docetaxel | 50 mg | 4.77 |
| 2 | Polyoxyl glyceryl fatty acid ester | LABRASOL ™ | 0.28 ml | 28.20 |
| 3 | Oleoyl glycerol complex | PECEOL ™ | 0.56 ml | 49.87 |
| 4 | Surfactant | Tween ™ 80 | 0.16 ml | 17.16 |
| | Total | | 100.00 |

Example 11

The docetaxel-containing pharmaceutical composition for oral administration in the soft capsule form was prepared in accordance with the same procedures as in Example 10, using Gelucire™ 44/14 (Gettafosse) instead of LABRASOL™.

Example 12

The docetaxel-containing pharmaceutical composition for oral administration in the soft capsule form was prepared in accordance with the same procedures as in Example 10, using Gelucire™ 50/13 (Gettafosse) instead of LABRASOL™.

Example 13

The docetaxel-containing pharmaceutical composition for oral administration in the soft capsule form was prepared in accordance with the same procedures as in Example 10, using Capmul™ GMO-50 EP/NF (Abitec) instead of PECEOL™.

Example 14

The docetaxel-containing pharmaceutical composition for oral administration in the soft capsule form was prepared in accordance with the same procedures as in Example 10, using methylene chloride instead of ethanol.

Example 15. Paclitaxel-Containing Soft Capsules

Figure 4:
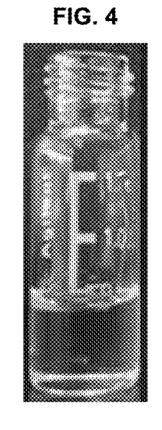
FIG. 4 represents the appearance of the paclitaxel-containing lipid solution prepared in Example 15.

The paclitaxel-containing pharmaceutical composition for oral administration was prepared according to the components and amounts shown in Table 5. Paclitaxel and LABRASOL™ (Gattefosse) were completely dissolved in methylene chloride (about 14 times of the volume of LABRASOL™). The resulting solution was dried under reduced pressure at 40° C. to remove methylene chloride. To the resulting mixture, were added PECEOL™ (Gattefosse) and Tween™ 80. The resulting mixture was stirred at 40° C. to obtain the clear oily solution. The resulting clear oily solution was filled into a soft capsule. The appearance of the oily solution is shown in FIG. 4.

TABLE 5

| L/I | Component | Amount/ 1 capsule | Ratio (% by weight) |
|---|---|---|---|
| 1 | Taxane | Paclitaxel | 100 mg | 9.10 |
| 2 | Polyoxyl glyceryl fatty acid ester | LABRASOL ™ | 0.28 ml | 26.91 |
| 3 | Oleoyl glycerol complex | PECEOL ™ | 0.56 ml | 47.61 |
| 4 | Surfactant | Tween ™ 80 | 0.16 ml | 16.38 |
| | Total | | 100.00 |

Example 16

The paclitaxel-containing pharmaceutical composition for oral administration in the soft capsule form was prepared in accordance with the same procedures as in Example 15, using anhydrous ethanol instead of methylene chloride.

Example 17

The paclitaxel-containing pharmaceutical composition for oral administration in the soft capsule form was prepared in accordance with the same procedures as in Example 15, using Gelucire™ 44/14 (Gettafosse) instead of LABRASOL™.

Example 18

The paclitaxel-containing pharmaceutical composition for oral administration in the soft capsule form was prepared in accordance with the same procedures as in Example 15, using Gelucire™ 50/13 (Gettafosse) instead of LABRASOL™.

Example 19

The paclitaxel-containing pharmaceutical composition for oral administration in the soft capsule form was prepared in accordance with the same procedures as in Example 15, using Capmul™ GMO-50 EP/NF (Abitec) instead of PECEOL™.

Example 20. Paclitaxel-Containing Soft Capsules

The paclitaxel-containing pharmaceutical composition for oral administration was prepared according to the components and amounts shown in Table 6. Paclitaxel and LABRASOL™ (Gattefosse) were completely dissolved in methylene chloride (about 14 times of the volume of LABRASOL™). The resulting solution was dried under reduced pressure at 40° C. to remove methylene chloride. To the resulting mixture, were added PECEOL™ (Gattefosse) and Tween™ 80. The resulting mixture was stirred at 40° C. to obtain the clear oily solution.

TABLE 6

| L/I | | Component | Amount/ 1 capsule | Ratio (% by weight) |
|---|---|---|---|---|
| 1 | Taxane | Paclitaxel | 500 mg | 34.09 |
| 2 | Polyoxyl glyceryl fatty acid ester | LABRASOL ™ | 0.28 ml | 17.99 |
| 3 | Oleoyl glycerol complex | PECEOL ™ | 0.56 ml | 36.26 |
| 4 | Surfactant | Tween ™ 80 | 0.16 ml | 11.66 |
| | | Total | | 100.00 |

Comparative Example 1

The paclitaxel-containing composition was prepared according to the components and amounts shown in Table 7. Paclitaxel and monooleoyl glycerol (Rylo MG 19™, Danisco) were completely dissolved in methylene chloride (about 14 times of the volume of monooleoyl glycerol). The resulting solution was dried under reduced pressure at 40° C. to remove methylene chloride. To the resulting mixture was added Tween™ 80. The resulting mixture was stirred at 40° C. to obtain the oily solution.

TABLE 7

| L/I | | Component | Amount/ 1 capsule | Ratio (% by weight) |
|---|---|---|---|---|
| 1 | Taxane | Paclitaxel | 70 mg | 6.49 |
| 2 | Monooleoyl glycerol | Rylo MG 19 ™ | 0.84 ml | 83.51 |
| 3 | Surfactant | Tween ™ 80 | 1.16 ml | 10.00 |
| | | Total | | 100.00 |

Figure 5:
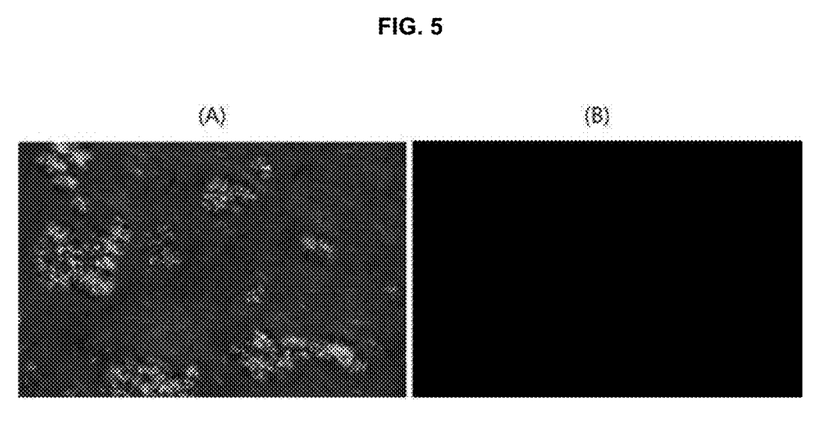
FIG. 5 represents the photographs of the paclitaxel-containing oily solutions obtained in Comparative Example 1 and Example 5, which were taken with a polarizing microscope. A: the paclitaxel-containing oily solution obtained in Comparative Example 1, B: the paclitaxel-containing oily solution obtained in Example 5.

The photographs of the oily solutions obtained in the above and Example 5 were taken with a polarizing microscope (Olympus CX41) at a resolution of 200 times. The results thereof are shown in FIG. 5. From the results of FIG. 5, it can be seen that the oily solution obtained according to the present invention is in a clear solution form having no precipitate, while the oily solution obtained in Comparative Example 1 is in a solution form having precipitates.

Comparative Example 2

The paclitaxel-containing composition was prepared according to the components and amounts shown in Table 8. Paclitaxel and PECEOL™ (Gattefosse) were completely dissolved in methylene chloride (about 14 times of the volume of PECEOL™) The resulting solution was dried under reduced pressure at 40° C. to remove methylene chloride. To the resulting mixture was added Tween™ 80. The resulting mixture was stirred at 40° C. to obtain the oily solution.

TABLE 8

| L/I | | Component | Amount/ 1 capsule | Ratio (% by weight) |
|---|---|---|---|---|
| 1 | Taxane | Paclitaxel | 50 mg | 9.1 |
| 2 | Oleoyl glycerol complex | PECEOL ™ | 0.84 ml | 74.9 |
| 3 | Surfactant | Tween ™ 80 | 1.16 ml | 16.00 |
| | | Total | | 100.00 |

Figure 6:
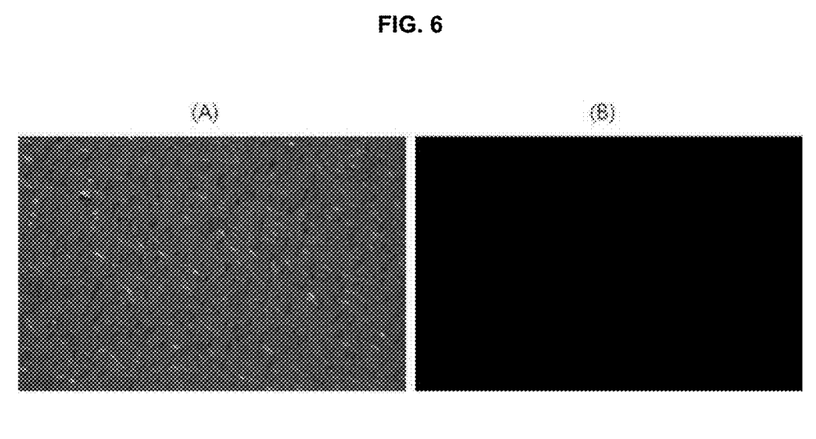
FIG. 6 represents the photographs of the paclitaxel-containing oily solutions obtained in Comparative Example 2 and Example 15, which were taken with a polarizing microscope. A: the paclitaxel-containing oily solution obtained in Comparative Example 2, B: the paclitaxel-containing oily solution obtained in Example 15.

The photographs of the oily solutions obtained in the above and Example 15 were taken with a polarizing microscope (Olympus CX41) at a resolution of 200 times. The results thereof are shown in FIG. 6. From the results of FIG. 6, it can be seen that the oily solution obtained according to the present invention is in a clear solution form having no precipitate, while the oily solution obtained in Comparative Example 2 is in a solution form having precipitates.

Experimental Example 1. Stability Evaluation of Gelatin Capsules

The soft capsules prepared in Examples 1, 5, 10, and 15 were placed in a HDPE bottle, which were then stored under the conditions of 25° C. and 60% (RH) for 6 months to evaluate the stability of the gelatin capsules. Stability of the gelatin capsules was evaluated through observing the appearances thereof and a leak therefrom. The results are shown in the following Table 9.

TABLE 9

| | | Example 1 | Example 5 | Example 10 | Example 15 |
|---|---|---|---|---|---|
| 1 month | Leak | No leak occurred | No leak occurred | No leak occurred | No leak occurred |
| | Appearance | No appearance changed | No appearance changed | No appearance changed | No appearance changed |
| 3 months | Leak | No leak occurred | No leak occurred | No leak occurred | No leak occurred |
| | Appearance | No appearance changed | No appearance changed | No appearance changed | No appearance changed |
| 6 months | Leak | No leak occurred | No leak occurred | No leak occurred | No leak occurred |
| | Appearance | No appearance changed | No appearance changed | No appearance changed | No appearance changed |

From the results of Table 9, it can be seen that the soft capsules prepared according to the present invention have excellent stability.

Experimental Example 2. Evaluation of In Vivo Absorption Rate

The docetaxel-containing oily solution prepared in Example 10 was orally administered in the doses of 240 mg/kg and 400 mg/kg to ICR mice (6 week old, female, Orient Bio, Republic of Korea), using a gastric zonde. At 0 minute, 15 minutes, 30 minutes, 1 hour, 2 hours, and 4 hours after the respective drug administration, the blood samples were taken from the orbital veins of the mice and then centrifuged at 8,000×g at 4° C. for 20 minutes to obtain the plasma samples, which were stored at −70° C.

The plasma samples were melted at room temperature and then stirred with a vortex mixer for 1 minute. The internal standard solution (paclitaxel 10 μg/mL, in acetonitrile) (200.0 μL) and acetonitrile (400.0 μL) were added to the plasma samples (200.0 μL), which were then stirred with a vortex mixer at 3,000 rpm for 5 minutes. Each samples were centrifuged at 14,000×g under the condition of 8° C. for 20 minutes. Each supernatant (300 μL) was taken therefrom and then filtered through syringe filter (PTFE, chromdisc, 13 mm, pore size 0.20 mm). The filtrate (200.0 μL) was taken therefrom and then subject to the HPLC analysis.

The conditions for HPLC analysis are as follows.
HPLC: Shimadzu LC-20AD
Detector: Shimadzu SPD-20A
Column: Shim-pack GIS, 5 μm ODS, 250×4.6 mm id.
Data processor: Labsolutions, Shimadzu
Injection volume: 100.0 μL
Flow rate: 1.0 mL/min
Column temperature: 40° C.
Detection wave length: 227 nm
Mobile phase: (A) ACN, (B) DW (ACN: acetonitrile, DW: distilled water)

| Time (minute) | Mobile phase (A) | Mobile phase (B) |
|---|---|---|
| 0 | 30 | 70 |
| 30 | 60 | 40 |
| 35 | 100 | 0 |
| 40 | 0 | 100 |
| 45 | 30 | 70 |

The pharmacokinetic parameters calculated from the blood concentrations of docetaxel measured in the above are shown in Table 10.

TABLE 10

|  | 240 mg/kg | 400 mg/kg |
|---|---|---|
| Cmax (μg/mL) | 4.1797 | 5.4843 |
| Tmax (hr) | 0.25 | 0.5 |
| $AUC_{0-4\ hr}$ (μg · hr/mL) | 3.7314 | 6.2478 |
| $AUC_{0-\infty}$ (μg · hr/mL) | 4.0814 | 6.457 |

From the results of Table 10, it can be seen that the pharmaceutical compositions according to the present invention were rapidly absorbed from the beginning and exhibited remarkably increased in vivo absorption rate.

Experimental Example 3. Evaluation of In Vivo Absorption Rate

The paclitaxel-containing oily solution prepared in Example 15 was orally administered in the doses of 500 mg/kg, 300 mg/kg, and 150 mg/kg to ICR mice (6 week old, female, Orient Bio, Republic of Korea), using a gastric zonde. At 0 minute, 15 minutes, 30 minutes, 1 hour, 2 hours, 4 hours, 6 hours, and 8 hours after the respective drug administration, the blood samples were taken from the orbital veins of the mice and then centrifuged at 8,000×g at 4° C. for 20 minutes to obtain the plasma samples, which were stored at −70° C.

The plasma samples were melted at room temperature and then stirred with a vortex mixer for 1 minute. The internal standard solution (docetaxel 10 μg/mL, in acetonitrile) (200.0 μL) and acetonitrile (400.0 μL) were added to the plasma samples (200.0 μL), which were then stirred with a vortex mixer at 3,000 rpm for 5 minutes. Each samples were centrifuged at 14,000×g under the condition of 8° C. for 20 minutes. Each supernatant (300 μL) was taken therefrom and then filtered through syringe filter (PTFE, chromdisc, 13 mm, pore size 0.20 mm). The filtrate (200.0 μL) was taken therefrom and then subject to the HPLC analysis, under the same conditions for HPLC analysis as in Experimental Example 1.

The pharmacokinetic parameters calculated from the blood concentrations of paclitaxel measured in the above are shown in Table 11.

TABLE 11

|  | 500 mg/kg | 300 mg/kg | 150 mg/kg |
|---|---|---|---|
| Cmax (μg/mL) | 0.7296 | 0.4460 | 0.3191 |
| Tmax (hr) | 0.25 | 0.25 | 0.25 |
| $AUC_{0-8\ hr}$ (μg · hr/mL) | 1.7176 | 0.3717 | 0.2318 |

From the results of Table 11, it can be seen that the pharmaceutical compositions according to the present invention were rapidly absorbed from the beginning and exhibited remarkably increased in vivo absorption rate.

The invention claimed is:

1. A pharmaceutical composition for oral administration, consisting essentially of
   (a) 4 to 40% by weight of paclitaxel or docetaxel,
   (b) 10 to 40% by weight of polyoxyl glyceryl fatty acid ester selected from the group consisting of caprylocaproyl polyoxyl glyceride, lauroyl polyoxyl glyceride, and stearoyl polyoxyl glyceride,
   (c) (c-1) 30 to 70% by weight of monooleoyl glycerol or
   (c-2) 30 to 70% by weight of an oleoyl glycerol complex having 30 to 65% by weight of monooleoyl glycerol contents; 15 to 50% by weight of dioleoyl glycerol contents; and 2 to 20% by weight of trioleoyl glycerol contents, and
   (d) 5 to 30% by weight of polyoxyethylene (80) sorbitan monooleate,
   wherein the pharmaceutical composition is in the form of a clear solution.

2. The pharmaceutical composition for oral administration according to claim 1, wherein the oleoyl glycerol complex has 32 to 52% by weight of monooleoyl glycerol contents; 30 to 50% by weight of dioleoyl glycerol contents; and 5 to 20% by weight of trioleoyl glycerol contents.

3. The pharmaceutical composition for oral administration according to claim 1, wherein the oleoyl glycerol complex has 55 to 65% by weight of monooleoyl glycerol contents; 15 to 35% by weight of dioleoyl glycerol contents; and 2 to 10% by weight of trioleoyl glycerol contents.

4. The pharmaceutical composition for oral administration according to claim 1, wherein the polyoxyl glyceryl fatty acid ester is one or more selected from the group consisting of caprylocaproyl polyoxyl-32 glyceride, lauroyl polyoxyl-32 glyceride, and stearoyl polyoxyl-32 glyceride.

5. The pharmaceutical composition for oral administration according to claim 1, consisting essentially of 4 to 35% by weight of paclitaxel or docetaxel, 15 to 30% by weight of the polyoxyl glyceryl fatty acid ester, 35 to 60% by weight of monooleoyl glycerol or the oleoyl glycerol complex, and 10 to 25% by weight of polyoxyethylene (80) sorbitan monooleate.

6. A process for preparing a pharmaceutical composition for oral administration, comprising
   (i) dissolving (a) 4 to 40% by weight of paclitaxel or docetaxel and (b) 10 to 40% by weight of polyoxyl glyceryl fatty acid ester selected from the group consisting of caprylocaproyl polyoxyl glyceride, lauroyl polyoxyl glyceride, and stearoyl polyoxyl glyceride in an organic solvent,
   (ii) removing the organic solvent from the solution obtained in Step (i), followed by mixing (c-1) 30 to 70% by weight of monooleoyl glycerol or (c-2) 30 to 70% by weight of an oleoyl glycerol complex having 30 to 65% by weight of monooleoyl glycerol contents; 15 to 50% by weight of dioleoyl glycerol contents; and 2 to 20% by weight of trioleoyl glycerol contents, and (d) 5 to 30% by weight of polyoxyethylene (80) sorbitan monooleate therewith to form a solution, and
   (iii) optionally, filling the solution obtained in Step (ii) in a capsule,
   wherein the pharmaceutical composition is in the form of a clear solution.

7. A process for preparing a pharmaceutical composition for oral administration, comprising
   (i') dissolving (a) 4 to 40% by weight of paclitaxel or docetaxel, (b) 10 to 40% by weight of polyoxyl glyceryl fatty acid ester selected from the group consisting of caprylocaproyl polyoxyl glyceride, lauroyl polyoxyl glyceride, and stearoyl polyoxyl glyceride, (c-1) 30 to 70% by weight of monooleoyl glycerol or (c-2) 30 to 70% by weight of an oleoyl glycerol complex having 30 to 65% by weight of monooleoyl glycerol contents; 15 to 50% by weight of dioleoyl glycerol contents; and 2 to 20% by weight of trioleoyl glycerol contents, and (d) 5 to 30% by weight of polyoxyethylene (80) sorbitan monooleate in an organic solvent,
   (ii') removing the organic solvent from the solution obtained in Step (i'), and
   (iii') optionally, filling the solution obtained in Step (ii') in a capsule,
   wherein the pharmaceutical composition is in the form of a clear solution.

8. The process according to claim 6, wherein the oleoyl glycerol complex has 32 to 52% by weight of monooleoyl glycerol contents; 30 to 50% by weight of dioleoyl glycerol contents; and 5 to 20% by weight of trioleoyl glycerol contents.

9. The process according to claim 6, wherein the oleoyl glycerol complex has 55 to 65% by weight of monooleoyl glycerol contents; 15 to 35% by weight of dioleoyl glycerol contents; and 2 to 10% by weight of trioleoyl glycerol contents.

10. The process according to claim 6, wherein the polyoxyl glyceryl fatty acid ester is one or more selected from the group consisting of caprylocaproyl polyoxyl-32 glyceride, lauroyl polyoxyl-32 glyceride, and stearoyl polyoxyl-32 glyceride.

11. The process according to claim 6, wherein the organic solvent is one or more selected from the group consisting of a halogenated alkyl compound, an alcohol, and a ketone.

12. The process according to claim 11, wherein the organic solvent is one or more selected from the group consisting of methylene chloride and ethanol.

13. The process according to claim 7, wherein the oleoyl glycerol complex has 32 to 52% by weight of monooleoyl glycerol contents; 30 to 50% by weight of dioleoyl glycerol contents; and 5 to 20% by weight of trioleoyl glycerol contents.

14. The process according to claim 7, wherein the oleoyl glycerol complex has 55 to 65% by weight of monooleoyl glycerol contents; 15 to 35% by weight of dioleoyl glycerol contents; and 2 to 10% by weight of trioleoyl glycerol contents.

15. The process according to claim 7, wherein the organic solvent is one or more selected from the group consisting of a halogenated alkyl compound, an alcohol, and a ketone.

\* \* \* \* \*